(12) United States Patent
Chen et al.

(10) Patent No.: US 12,122,760 B2
(45) Date of Patent: Oct. 22, 2024

(54) COMPOUND, COMPOSITION, AND USE THEREOF IN PREPARATION OF DRUG

(71) Applicant: CHANGSHA ZEDA MEDICAL TECH. CO., LTD, Changsha (CN)

(72) Inventors: Yongheng Chen, Changsha (CN); Guangyu Xu Chen, Changsha (CN); Wenqiang Zhou Chen, Changsha (CN)

(73) Assignee: CHANGSHA ZEDA MEDICAL TECH CO., LTD, Changsha (CN)

( * ) Notice: Subject to any disclaimer, the term of this patent is extended or adjusted under 35 U.S.C. 154(b) by 968 days.

(21) Appl. No.: 17/136,176

(22) Filed: Dec. 29, 2020

(65) Prior Publication Data

US 2021/0115014 A1    Apr. 22, 2021

Related U.S. Application Data

(63) Continuation-in-part of application No. PCT/CN2019/082441, filed on Apr. 12, 2019.

(51) Int. Cl.
| | | |
|---|---|---|
| *C07D 401/04* | (2006.01) | |
| *A61P 35/00* | (2006.01) | |
| *C07D 233/86* | (2006.01) | |
| *C07D 235/02* | (2006.01) | |

(52) U.S. Cl.
CPC ............ *C07D 401/04* (2013.01); *A61P 35/00* (2018.01); *C07D 233/86* (2013.01); *C07D 235/02* (2013.01)

(58) Field of Classification Search
None
See application file for complete search history.

(56) References Cited

FOREIGN PATENT DOCUMENTS

| CN | 101048381 A | 10/2007 |
|---|---|---|
| CN | 101222922 A | 7/2008 |
| CN | 101454002 A | 6/2009 |
| CN | 108976171 A | 12/2018 |

*Primary Examiner* — Jeffrey S Lundgren
*Assistant Examiner* — Michael J Schmitt

(57) ABSTRACT

The disclosure relates to a compound, having a structure of Formula I or a pharmaceutically acceptable salt thereof, herein, R1 is selected from hydrogen, fluorine, and chlorine; R2 and R3 are independently selected from hydrogen, alkyl, a substituted alkyl, alkenyl or a substituted alkenyl, alkynyl or a substituted alkynyl, and aryl, or R2 and R3 are connected to form a ring selected from a cycloalkyl, a substituted cycloalkyl, an aromatic heterocycle or a non-aromatic heterocycle; R4 is selected from hydrogen, cyano, alkyl, a substituted alkyl, alkenyl or a substituted alkenyl, alkynyl or a substituted alkynyl, and aryl; and R5 is selected from hydrogen, halogen, and haloalkyl. The disclosure further relates to a pharmaceutical composition containing the compound. The compound and the composition of the disclosure show significant activity in an aspect of treating AR-prostate cancer and triple-negative breast cancer.

11 Claims, 5 Drawing Sheets

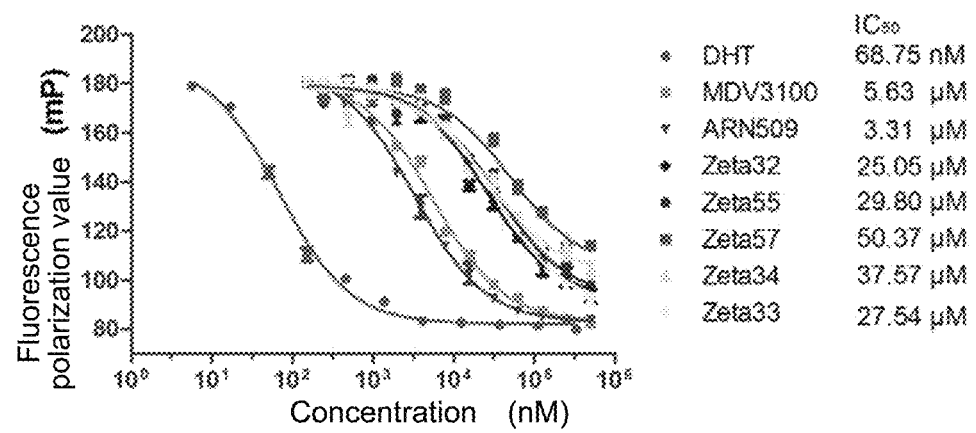
Fig. 1 The IC$_{50}$ result of the drug and AR-LBD binding
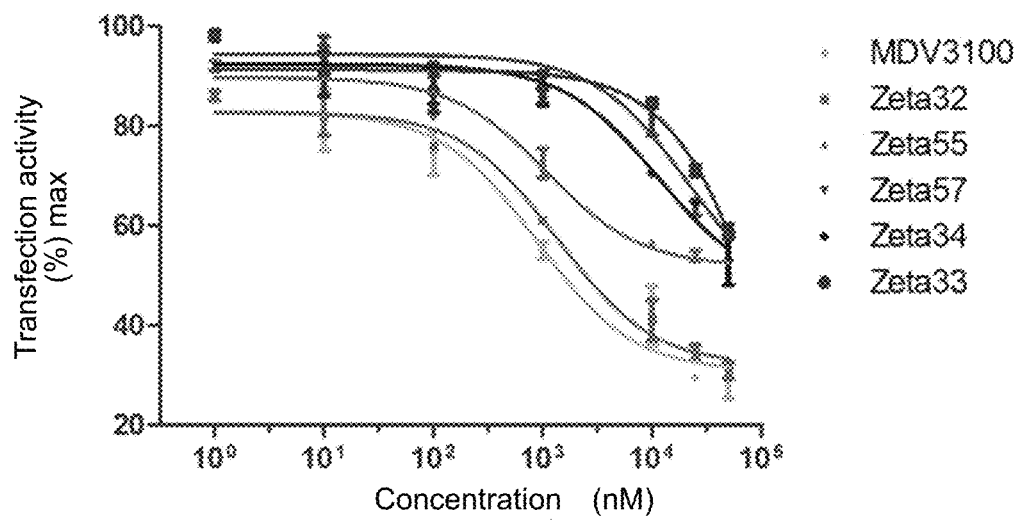
Fig. 2 Luciferase reporter gene experiment of the drugs

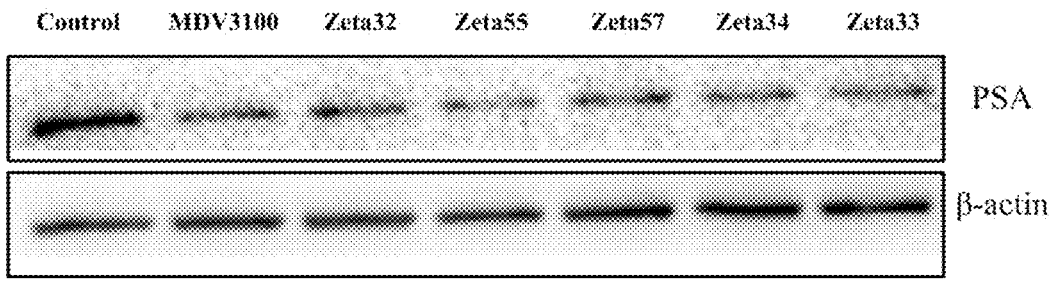
Fig. 3 Effect of the drug on expression of the AR-activated downstream protein (PSA) in the VCaP cell
Fig. 4 Effect of the drug on the tubulin acetylation.
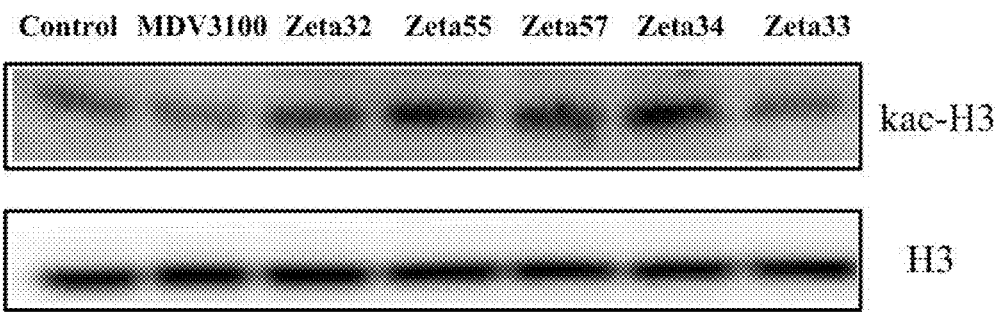
Fig. 5 Effect of the drug on the histone H3 acetylation.

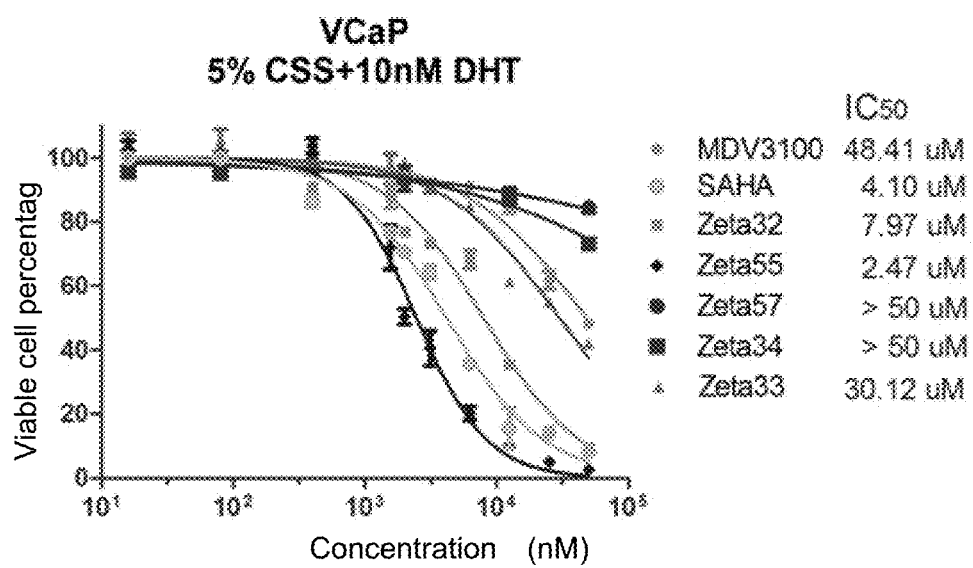
Fig. 6 Anti-proliferative effect of the drug on the VCaP cell.
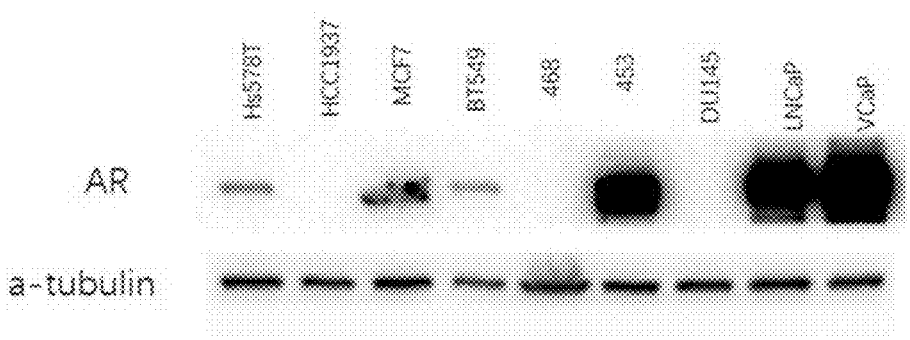
Fig. 7

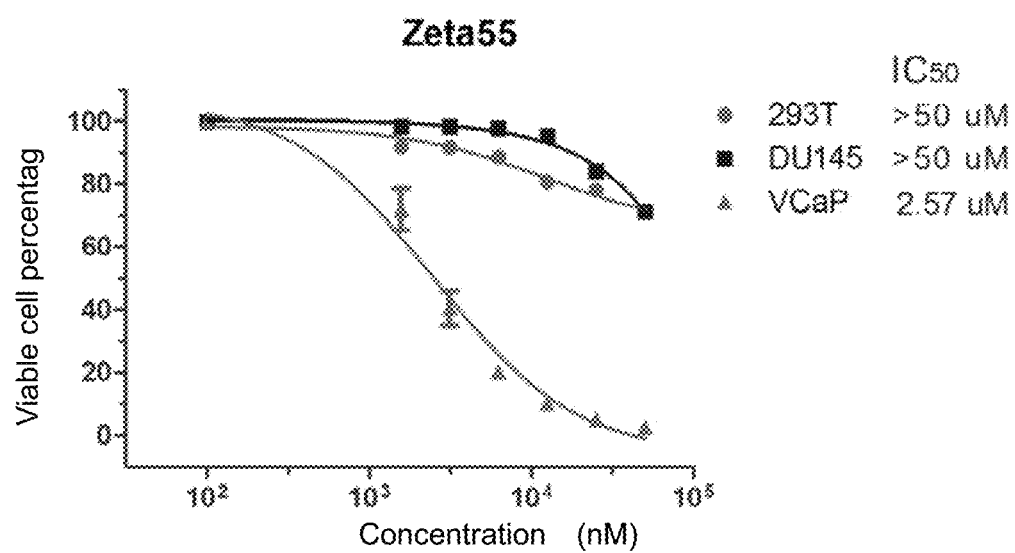
Fig 10. Selectivity of Zeta 55 to inhibit proliferation of three types of cells after 4 days of treatment

COMPOUND, COMPOSITION, AND USE THEREOF IN PREPARATION OF DRUG

TECHNICAL FIELD

The disclosure relates to a new-type antagonist compound of an androgen receptor, a method for treating diseases related to the androgen receptor, such as prostate cancer, by using the compound, and a pharmaceutical composition containing the compound.

BACKGROUND

Androgen receptor (AR) is a ligand-dependent transcriptional regulatory protein, and belongs to a nuclear receptor superfamily member. The binding of androgen receptor with an androgen, such as a testosterone or a more effective dihydrotestosterone (DTH), causes conformational change, resulting in the androgen receptor activation. The activated androgen receptor, in the form of dimer, combines with androgen reaction element (ARE), a specific DNA sequence in target cell nucleus, regulating the expression of a target gene, and resulting in corresponding biological effects to proliferation, survival and differentiation of cells. The androgen receptor plays an important role in many male hormone-related diseases. For example, the prostate cancer is highly sensitive to the androgen and a prostate cancer cell is characterized by high expression of the androgen receptor. In addition, AR also stimulates cell proliferation of triple-negative breast cancer.

Prostate cancer is the most common malignant tumor of male reproductive system. Many aged men eventually suffer from prostate cancer with microscopic symptoms. Compared with other malignant tumors, the growth of prostate cancer is quite slow, 90% of prostate cancer patients remain a latent state for decades without obvious clinical symptoms. Like many other cancers, it will continuously develop and then spread to other tissues via blood or lymph, if not treated at the initial stage.

At present, androgen receptor antagonist (AR Antagonist) is a main chemical drug for treating prostate cancer. The clinically-approved androgen receptor antagonist (AR Antagonist) (i.e. Bicalutamide, Enzalutamide and Apalutamide) can clinically slow down the development of prostate cancer, by directly preventing testosterone or dihydrotestosterone (DHT) from binding with androgen receptor, thereby interdicting the physiological effect of androgen. However, the ability of above-mentioned drugs to directly kill prostate cancer cells is not significant, with IC50 higher than 10 uM in cell biology experiments and their total effective rate to triple-negative breast cancer is less than 50%.

Therefore, there is still needs in this present field to keep on searching compounds that have the ability to selectively kill prostate cancer cells with high expression of androgen receptors, so as to overcome the hormone-refractory prostate cancer and to avoid or slow down the development of hormone-sensitive prostate cancers.

SUMMARY

According to this disclosure, a type of compounds is provided to regulate the function of nuclear hormone receptors, particularly the function of androgen receptors. These compounds can cause disappearance of cancer cells and the tumors.

The compound of the disclosure has the structure of Formula I:

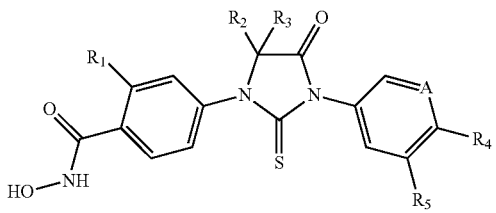

Formula I wherein, R1 is selected from hydrogen, fluorine, and chlorine; R2 and R3 are independently selected from a hydrogen, an alkyl, a substituted alkyl, an alkenyl or a substituted alkenyl, an alkynyl or a substituted alkynyl, and an aryl, or the R2 and R3 are connected to form a ring, which is selected from a cycloalkyl, a substituted cycloalkyl, an aromatic heterocycle or a non-aromatic heterocycle; R4 is selected from hydrogen, cyano, alkyl, substituted alkyl, alkenyl or substituted alkenyl, alkynyl or substituted alkynyl, and aryl; and R5 is selected from hydrogen halogen, and haloalkyl.

In an embodiment of the present invention, R1 is the hydrogen or the fluorine.

In an embodiment of the present invention, R2 and R3 are independently an alkyl of C1-03, or combined to form a cycloalkyl of C3-C6.

In an embodiment of the present invention, R4 is cyano.

In an embodiment of the present invention, R5 is trihalomethyl, preferably trifluoromethyl.

In the synthesis embodiments of the disclosure, the following compounds are synthesized:

4-(3-(4-cyano-3-(trifluoromethyl)phenyl)-5,5-dimethyl-4-oxo-2-thioimidazolidine-1-yl)-2-fluoro-N-hydroxybenzamide

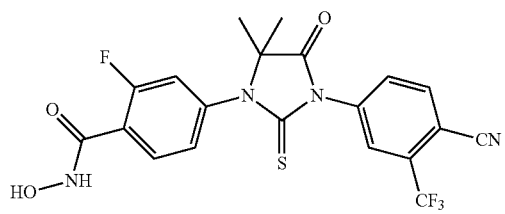

Zeta 32

4-(3-(6-cyano-5-(trifluoromethyl)pyridin-3-yl)-5,5-dimethyl-4-oxo-2-thioimidazolidine-1-yl)-2-fluoro-N-hydroxybenzamide

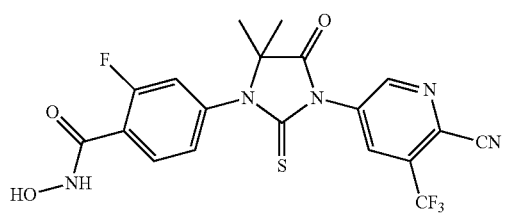

Zeta 33

4-(3-(3-chloro-4-cyanophenyl)-5,5-dimethyl-4-oxo-2-thioimidazolidine-1-yl)-2-fluoro-N-hydroxybenzamide Zeta 34

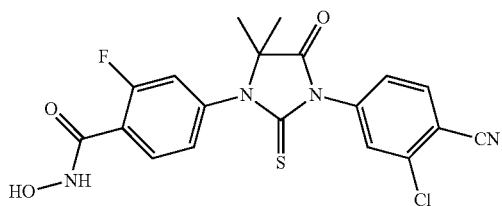

4-(7-(4-cyano-3-(trifluoromethyl)phenyl)-8-oxo-6-thio-5,7-diazaspiro[3.4]octane-5-yl)-2-fluoro-N-hydroxybenzamide Zeta 55

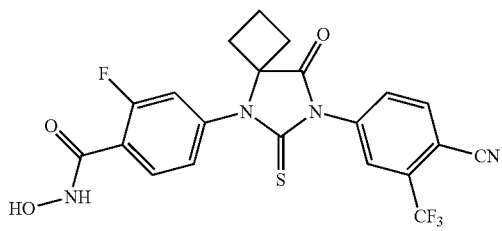

4-(7-(6-cyano-5-(trifluoromethyl)pyridin-3-yl)-8-oxo-6-thio-5,7-diazaspiro[3.4]octane-5-yl)-2-fluoro-N-hydroxybenzamide Zeta 57

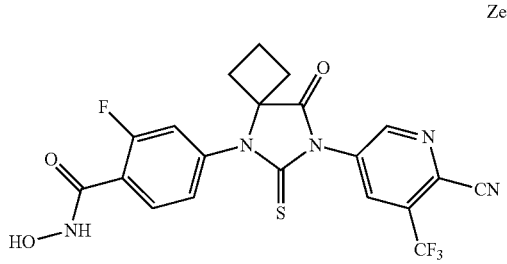

In an implementation scheme, a pharmaceutical composition includes a therapeutically effective amount of the compound or the pharmaceutically acceptable salt thereof, and pharmaceutically acceptable carrier, diluent or additive.

The pharmaceutical composition may include solution of dimethyl sulfoxide, carboxymethyl cellulose, polysorbate and water.

A method embodiment of the invention refers to preventing or treating hyper-proliferative disorders such as triple-negative breast cancer, hormone-sensitive prostate cancer and hormone-refractory prostate cancer, and may include administering a patient suffering from the disorders the compound according to Formula I or the pharmaceutically acceptable salts thereof, for the treatment or prevention of the hyperproliferative disorders. The compound may be administered by compact injection administration, tissue injection administration, intraperitoneal administration, or oral administration.

In an implementation, the compound of Formula I has a strong affinity with the androgen receptor (AR), and may inhibit expression of a downstream protein of an AR pathway. The compound of Formula I has obvious histone deacetylase inhibitory activity. It has a significant inhibitory effect on proliferation of a tumor cell with high expression of the androgen receptor.

BRIEF DESCRIPTION OF THE DRAWINGS

FIG. 1: the $IC_{50}$ result of the drug and AR-LBD binding.
FIG. 2: Curve of the result of the luciferase reporter gene experiment of the drug.
FIG. 3: Effect of the drug to expression of the AR-activated downstream protein in the VCaP cell.
FIG. 4: Effect of the drug on the tubulin acetylation.
FIG. 5: Effect of the drug on the histone H3 acetylation.
FIG. 6: Anti-proliferative effect of the drug on the VCaP cell.
FIG. 7: High level AR expression of TNBC cell line MDA-MB-453.
FIG. 10: Selectivity of Zeta 55 to inhibit proliferation of three types of cells after 4 days of treatment.

DETAILED DESCRIPTION OF THE EMBODIMENTS

Figure 8:
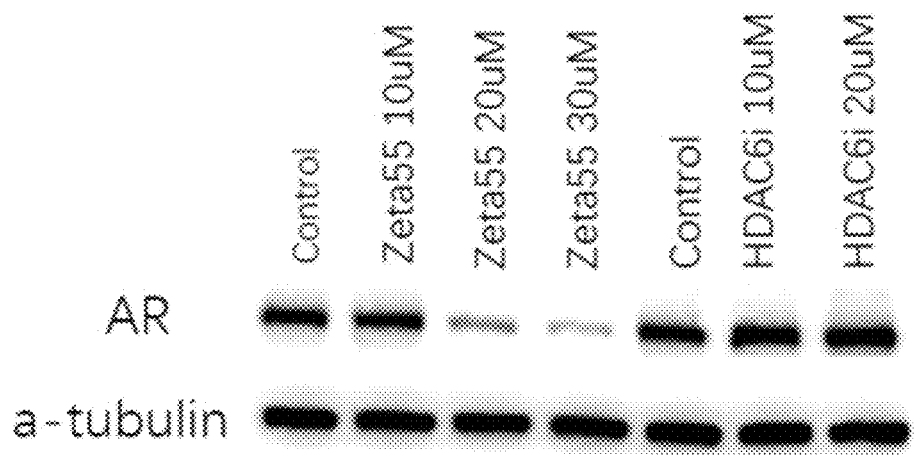
FIG. 8 and FIG. 9: Effect of Zeta55 on MDA-MB-453 TNBC cells.

The compound of the disclosure has a structure of Formula I:

Formula I

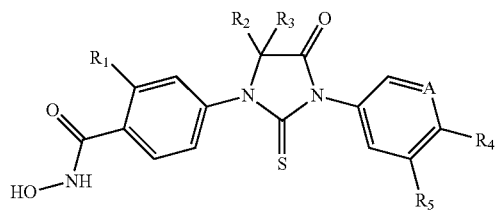

wherein, R1 is selected from hydrogen, fluorine, and chlorine; R2 and R3 are independently selected from the hydrogen, an alkyl, a substituted alkyl, an alkenyl or a substituted alkenyl, an alkynyl or a substituted alkynyl, and an aryl, or the R2 and R3 are connected to form a ring, which is selected from the ring may be a cycloalkyl, a substituted cycloalkyl, an aromatic heterocycle or a non-aromatic heterocycle; R4 is selected from the hydrogen, a cyano, the alkyl, the a substituted alkyl, the alkenyl or the substituted alkenyl, the alkynyl or the substituted alkynyl, and the aryl; and R5 is selected from the hydrogen, a halogen, and a haloalkyl.

The term "alkyl" used in the invention means a branched or straight hydrocarbon chain, preferably having about 1 to about 5 carbons, such as a methyl, an ethyl, an n-propyl, an isopropyl, an n-butyl, a sec-butyl, an isobutyl, a tert-butyl, a 2-methylpentyl, and a pentyl. The "substituted alkyl" means that the above alkyl is optionally substituted by one or more functional groups such as a hydroxyl, bromine, fluorine, chlorine, iodine, mercapto or thio, a cyano, an alkylthio, a heterocyclyl, an aryl, a heteroaryl, a carboxyl, an alkoxycarbonyl (carbalkoyl), an alkyl, an alkenyl, a nitro, an amino, an alkoxy, and an amido to form the alkyl such as a trifluoromethyl, a 3-hydroxyhexyl, a 2-carboxypropane, a 2-fluoroethyl, a carboxymethyl, and a cyanobutyl.

Unless otherwise specified, the term "cycloalkyl" used in the present article alone or as a part of another group includes a saturated or partially unsaturated (containing one or more double-bonds) cyclic hydrocarbon group containing 1 to 2 rings, preferably including 3 to 10 carbons, such as a cyclopropyl, a cyclobutyl, a cyclopentyl, a cyclohexyl, a cycloheptyl, a cyclooctyl, and a cyclodecyl. The "substituted cycloalkyl" includes the cycloalkyl, it is optionally substituted by one or more substituents such as a halogen, an alkyl, an alkoxy, a hydroxy, an aryl, an aryloxy, an arylalkyl, a cycloalkyl, an alkyl amido, an alkanoylamino, an oxo, an acyl, an arylcarbonylamino, an amino, a nitro, a cyano, a thiol and/or an alkylthio and/or any substituents included in definitions of the "substituted alkyl".

Unless otherwise specified, the term "alkenyl" used in the present article alone or as a part of another group refers that there are 2 to 10 carbons, preferably 2 to 8 carbons, and more preferably 2 to 5 carbons in a normal chain and the normal chain includes one or more double-bond straight or branched groups, such as a vinyl, a 2-propenyl, a 3-butenyl, a 2-butenyl, a 4-pentene, a 3-pentenyl, a 2-hexenyl, a 3-hexenyl, a 2-heptenyl, a 3-heptenyl, a 4-heptenyl, a 3-octenyl, a 3-nonenyl, and a 4-decenyl. The "substituted alkenyl" includes the alkenyl, it is optionally substituted by one or more substituents such as the above substituents included in definitions of "substituted alkyl" and "substituted cycloalkyl".

Unless otherwise specified, the term "alkynyl" used in the present article alone or as a part of another group refers that there are 2 to 8 carbons in the normal chain and the normal chain includes one or more triple-bond straight or branched groups, such as a 2-propynyl, a 3-butynyl, a 2-butynyl, a 4-pentynyl, a 3-pentynyl, a 2-hexynyl, a 3-hexynyl, a 2-heptynyl, a 3-heptynyl, a 4-heptynyl, and a 3-octynyl. The "substituted alkynyl" includes the alkynyl, it is optionally substituted by one or more substituents such as the above substituents included in definitions of the "substituted alkyl" and the "substituted cycloalkyl".

Unless otherwise specified, the term "aryl" or "Ar" used in the present article alone or as a part of another group refers to monocyclic and polycyclic aromatic groups (such as a phenyl or a naphthyl, including 1-naphthyl and 2-naphthyl) containing 6 to 10 carbons in a ring portion and one to three additional rings fused to a carbocyclic ring or a heterocyclic ring (such as an aryl, a cycloalkyl, a heteroaryl or a cycloheteroalkyl ring) are optionally included.

The "substituted aryl" includes the above aryl optionally substituted by one or more functional groups such as a halo, an alkyl, a haloalkyl, an alkoxy, a haloalkoxy, an alkenyl, a trifluoromethyl, a trifluoromethoxy, an alkynyl, a cycloalkyl, a cycloalkylalkyl, a hydroxy, a nitro, an cyano, and an amino (herein the amino includes the amino substituted by 1 or 2 alkyls).

Unless otherwise specified, the term "heterocycle" or "heterocycle" used in the present article refers to an unsubstituted or substituted stable 5- to 10-membered monocyclic ring system, it may be saturated or unsaturated, and formed by carbon atoms and 1 to 4 heteroatoms selected from N, O, or S, and herein the nitrogen and sulfur heteroatoms may be optionally oxidized, and the nitrogen heteroatoms may be optionally quaternized. For example, such heterocyclic groups include a piperidinyl, a piperazinyl, an oxypiperazinyl, a pyrrolyl, a pyrrolidinyl, a furyl, a thienyl, a pyrazolyl, a pyrazolidinyl, and an imidazolyl.

The compound of Formula I may exist as a pharmaceutically acceptable salt, which is also within a scope of the disclosure. If the compounds of Formula I have, for example, at least one basic center, they may form acid addition salts. These are, for example, formed by using a strong inorganic acid, a strong organic carboxylic acid or an organic sulfonic acid, the strong inorganic acid is a mineral acid such as a sulfuric acid, a phosphoric acid, or a halogen acid, the strong organic carboxylic acid is an unsubstituted or substituted (for example, substituted by the halogen) alkane carboxylic acid with 1 to 4 carbon atoms, such as an acetic acid, saturated or unsaturated dicarboxylic acids (such as an oxalic acid, a malonic acid, a succinic acid, a maleic acid, a fumaric acid, a phthalic acid or a terephthalic acid), hydroxycarboxylic acids (such as an ascorbic acid, a glycolic acid, a lactic acid, a malic acid, a tartaric acid or a citric acid), amino acids (such as an aspartic acid or a glutamic acid or a lysine or an arginine), or a benzoic acid, the organic sulfonic acid is formed by an unsubstituted or substituted (for example, substituted by the halogen) (C1-C4) alkyl or aryl sulfonic acid such as a methyl or p-toluene-sulfonic acid. If necessary, a basic center may also be derived additionally to form the corresponding acid addition salt.

The compound of the disclosure may be used in the form of a pharmaceutical composition, herein it contains a therapeutically effective amount of the compound of the disclosure as defined in the present article and a pharmaceutically acceptable carrier or diluent.

The form of the pharmaceutical composition according to the disclosure may be adjusted to be suitable for administering to patients in need of treatment such as mammals (for example, a human patient) by a variety of administration routes, such as oral administration, intranasal administration, intraperitoneal administration, or parenteral administration, administration by intravenous, intramuscular, topical or subcutaneous routes, or tissue injection administration. Such composition and preparation should contain at least 0.01% of one or more compounds of the disclosure. The percentages of the composition and preparation may be vary certainly and may, for example, be about 0.05% to about 2% by weight of a given unit dosage form. The amount of the compound in this therapeutically useful composition is such that an effective dosage level is obtained.

The compound of the disclosure may be administered systemically, such as orally, in combination with the pharmaceutically acceptable carriers such as an inert diluent or an assimilable edible carrier, or by inhalation or insufflation. They may be packaged in hard- or soft-shell capsules, may be compressed into tablets, or may be mixed directly with foods eaten by the patients. For the oral therapeutic administration, the compound of the disclosure may be combined with one or more excipients and used in the form of ingestible tablets, buccal tablets, lozenges, capsules, elixirs, suspensions, syrups, wafers and the like. The compound may be combined with a fine inert powdered carrier and inhaled or insufflated by the patients. Such composition and preparation should contain at least 0.1% of one or more compounds of the disclosure.

Tablets, lozenges, pills, capsules and the like may also contain: binders such as tragacanth, acacia, corn starch or gelatin; excipients such as dicalcium phosphate; disintegrants such as corn starch, potato starch, and an algae acid; lubricants such as magnesium stearate; and sweeteners such as sucrose, fructose, lactose or aspartame, or fragrances such as peppermint, wintergreen oil or cherry flavoring may be added. When the unit dosage form is a capsule, in addition to the above types of materials, it may also contain a liquid carrier such as vegetable oil or polyethylene glycol. Various other materials may exist as a coating or a physical form for modifying the solid unit dosage form in other modes. For example, the tablets, the pills, or the capsules may be coated with gelatin, wax, shellac, sugar and the like. The syrups or elixirs may contain active compounds, sucrose or fructose as the sweeteners, methyl paraben and propyl paraben as preservatives, dyes, and flavoring agents such as cherry or orange flavors. Certainly, any material used to prepare any unit dosage forms should be pharmaceutically acceptable and substantially non-toxic in amount. In addition, the compound of the disclosure may be incorporated into sustained release formulations and devices. For example, the compound may be introduced into a time release capsule, a time release tablet, and a time release pill.

The compound of the disclosure may also be administered intravenously or intraperitoneally by infusion or injection. Solution of the compound may be prepared in water, optionally mixed with a non-toxic surfactant. Pharmaceutical dosage forms suitable for injection or infusion may include sterile aqueous solution or dispersions or sterile powder. The liquid carrier may be a solvent or a liquid medium, including, for example, water, ethanol, polyol (for example, glycerol, propylene glycol, and liquid polyethylene glycol), vegetable oil, non-toxic glyceride, and suitable mixtures thereof.

For the topical administration, the compound of the disclosure may be used in pure form. However, it is generally expected to administer them to a skin as the compositions or the preparations together with a dermatologically acceptable carrier which may be solid or liquid.

Useful solid carriers include finely divided solid such as talc, clay, microcrystalline cellulose, silica, and alumina. Other solid carriers include non-toxic polymer nanoparticles or microparticles. Useful liquid carriers include water, alcohols or glycols or water/alcohol/glycol blends, herein the compound of the disclosure may be dissolved or dispersed at effective levels, optionally with the aid of non-toxic surfactants. Additives such as fragrances and additional antimicrobial agents may be added to optimize performance for a given application. The obtained liquid composition can be applied by an absorbent pad, used to impregnate a bandage and other dressings, or sprayed onto an affected area by using a pump-type or aerosol sprayer.

Thickeners such as a synthetic polymer, a fatty acid, fatty acid salt and ester, a fatty alcohol, modified cellulose or modified mineral material may also be used with the liquid carriers to form spreadable pastes, gels, ointments, soaps and the like, for direct application to the skin of a user.

The concentration of the compound in a liquid composition such as a lotion may be about 0.1 to about 25% by weight, or about 0.5 to about 10% by weight. The concentration in a semi-solid or solid composition such as a gel or powder may be about 0.1 to about 5% by weight, or about 0.5 to about 2.5% by weight.

The amount of the compound of the disclosure required for treatment is not only changed with the specific salt selected, but also changed with the route of administration, the nature of a condition being treated, age and condition of the patient, and is finally determined by an attending physician or a clinician.

The effective dosage and route of the administration of an agent of the disclosure are conventional. The precise amount (effective dose) of the agent is changed because of the different patients, depending on, for example, the type, age, weight and general or clinical state of the patient, the severity or mechanism of any diseases being treated, the specific agent or carrier used, and method and progress of the administration. The therapeutically effective dose may be empirically determined by routine procedures known to those skilled in the art.

Generally, a suitable dosage may be about 0.01 to about 500 mg/kg/day, such as about 0.1 to about 500 mg/kg body weight/day, such as about 0.1 to about 100 mg/kg recipient body weight/day. For example, the suitable dosage may be about 1 mg/kg, 10 mg/kg or 50 mg/kg body weight/day.

The compound of the disclosure is conveniently administered in the unit dosage form; for example, each unit dosage form contains about 0.0005 to about 500 mg, about 0.01 to about 50 mg, about 0.05 to about 10 mg, or about 5 mg of an active ingredient.

The compound of the disclosure may be administered to achieve a plasma concentration peak of, for example, about 0.5 to about 75 µM, about 1 to 50 µM, about 2 to about 30 µM, or about 5 to about 25 µM. Exemplary expected plasma concentrations include at least or no more than 0.25, 0.5, 1, 5, 10, 25, 50, 75, 100, or 200 µM. This may be achieved, for example, by the intravenous injection of 0.05-5% solution (optionally in saline) of the compound of the disclosure, or the oral administration in a bolus containing about 1-1000 mg of the compound. An expected blood level may be maintained by continuous infusion to provide about 0.0005 to about 25 mg/kg body weight/hour, for example at least or no more than 0.0005, 0.005, 0.05, 0.5, 5, or 25 mg/kg/hour. Alternatively, such level may be obtained by intermittent infusion containing about 0.002 to about 100 mg/kg body weight, for example at least or no more than 0.002, 0.02, 0.2, 2, 20, 50, or 100 mg compound/kg body weight.

The compound of the disclosure may be conveniently supplied as a single dose or as divided doses administered at appropriate intervals, for example as 2, 3, 4 or more sub-dose/day. The sub-dose itself may be further divided into a number of discrete loosely divided administrations; for example, multiple inhalations from an insufflator.

Example 1

Synthesis of 4-(3-(4-cyano-3-(trifluoromethyl)phenyl)-5,5-dimethyl-4-oxo-2-thioimidazolidine-1-yl)-2-fluoro-N-hydroxybenzamide (Compound Zeta 32)

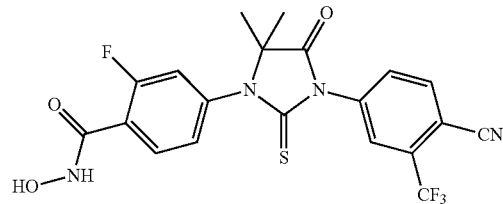

Zeta 32

(1) Synthesis of 4-(2-carboxypropyl-2-yl)amino)-2-fluorobenzoic acid 15

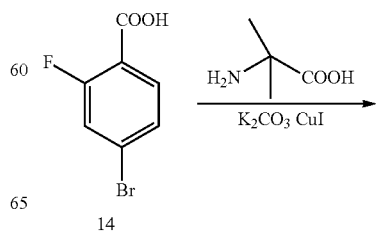

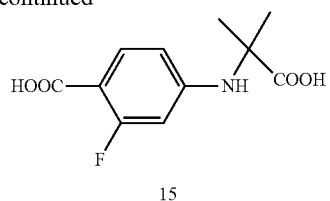

Into a 150 mL two-necked flask 2-fluoro-4-bromobenzoic acid (4.00 g, 18 mmol), 2-methyl-2-aminopropionic acid (2.78 g, 27 mmol), potassium carbonate (6.67 g, 48 mmol), CuI (0.45 g, 2.4 mmol), acetylacetone (1.44 g, 14.4 mmol), 30 mL of DMF, 2 mL of water and 3 drops of triethylamine are successively added, Under nitrogen protection, the reaction is performed at 140° C. for 24 h, monitored by TLC (ethyl acetate:petroleum ether=1:1). When the reaction finished, 20 mL of water is added, concentrated hydrochloric acid is added to adjust pH to 4, ethyl acetate (30×3 mL) is used for extracting, and anhydrous sodium sulfate is used for drying, the solvent is removed under reduced pressure, the residue is heated to dissolve by adding 20 mL of isopropanol, then cooled and crystallized, and filtered to obtain the compound 15 (3.47 g, brown solid) with a yield of 80.1%.

(2) Synthesis of 2-fluoro-4-((1-methoxy-2-methyl-1-oxopropane-2-yl) amino)methyl benzoate 16

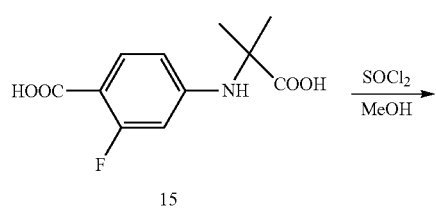

In a 150 mL two-necked flask, Compound 15 (5.00 g, 20.7 mmol) and 40 mL of methanol are added, 4.2 mL (58 mmol) of thionyl chloride is dropwise added under ice bath, then the temperature is risen to 80° C. for refluxing and stirring, the reaction is performed for 2 hours, then cooled to room temperature. 20% sodium carbonate solution is added to adjust a pH to 8, the mixture is extracted with ethyl acetate (30×3 mLg, washed with saturated sodium chloride solution, and dried with anhydrous sodium sulfate. Then solvent is removed under a reduced pressure to obtain the compound 16 (4.97 g, brown solid) with a yield of 95.6%.

(3) Synthesis of 4-(3-(4-cyano-3-(trifluoromethyl) phenyl)-5,5-dimethyl-4-oxo-2-thioimidazolidine-1-yl)-2-methyl fluorobenzoate 17

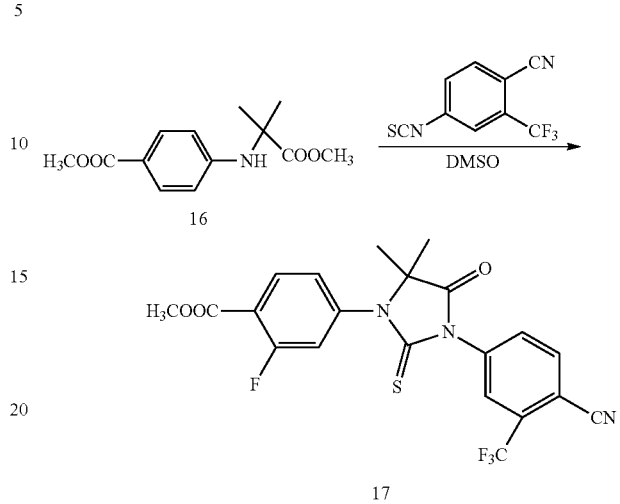

In a 50 mL two-necked flask, the compound 16 (1.00 g, 4.0 mmol), 4-isothiocyano-2-trifluoromethyl benzonitrile (1 g, 57.6 mmol), 1 mL of DMSO, and 10 mL of ethyl acetate are successively added, the reaction is performed at 85° C., monitored by TLC (petroleum ether:ethyl acetate=3:1). after the reaction is completed, 10 mL water is added, the mixture is extracted with ethyl acetate (20×3 mL), washed with saturated sodium chloride solution, dried with anhydrous sodium sulfate, and then solvent removed under reduced pressure. The residue is heated to dissolve by adding 10 mL of isopropanol, cooled and crystallized, and filtered to obtain the compound 17 (1.1 g, pale yellow solid) with a yield of 60.1%.

(4) Synthesis of 4-(3-(4-cyano-3-(trifluoromethyl) phenyl)-5,5-dimethyl-4-oxo-2-thioimidazolidine-1-yl)-2-fluorobenzoic acid 19

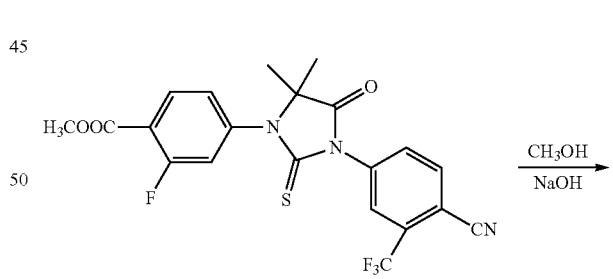

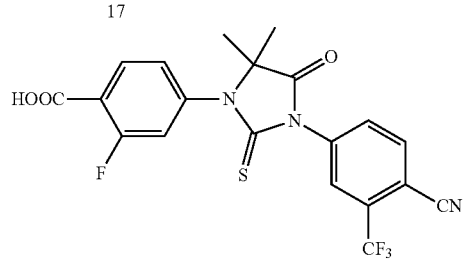

In a 150 mL two-neck flask, Compound 17 (3 g, 6.45 mmol), 25 mL of methanol and 25 mL of 1 mol/L sodium hydroxide solution are added, stirring is performed at 20° C. for 4 h, after a reaction is completed, 2 mol/L of a dilute hydrochloric acid is added to adjust a pH to 4. The mixture is extracted with ethyl acetate (50×3 mL), dried with anhydrous sodium sulfate, and solvent is removed under a reduced pressure to obtain the compound 19 (pale yellow solid, 2.86 g) with a yield of 98.2%.

(5) Synthesis of 4-(3-(4-cyano-3-(trifluoromethyl)phenyl)-5,5-dimethyl-4-oxo-2-thioimidazolidine-1-yl)-2-fluoro-N-hydroxybenzamide 20

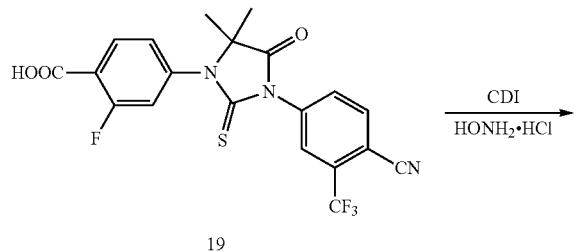

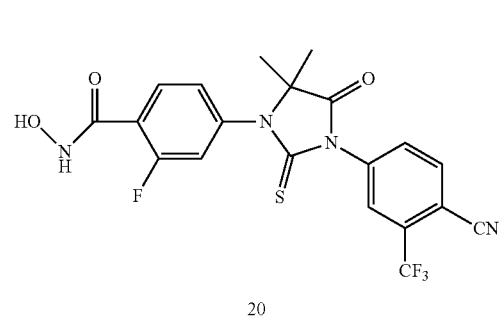

In a 25 mL two-necked flask, Compound 19 (0.5 g, 1.1 mmol), 8 mL of THF and CDI (0.357 g, 2.2 mmol) are added, after stirring is performed at 30° C. for 10 h, hydroxylamine hydrochloride (0.230 g, 3.3 mmol) is added. The reaction is performed at the room temperature for 10 h, monitored by TLC (ethyl acetate:petroleum ether:methanol=20:5:2). After the reaction completed, 8 mL of the water is added, the ethyl acetate (10×3 mL) is used for extracting, the anhydrous sodium sulfate is used for drying, and the solvent is removed under a reduced pressure. The residue is purified by silica gel column chromatography to obtain the compound Zeta 32 (0.144 g, pale yellow solid) with a yield of 28.1%.

M.W.: 466.41; $^1$H NMR (500 MHz, DMSO-d$_6$): δ 11.16 (s, 1H), 9.34 (s, 1H), 8.41 (d, J=10.0 Hz, 1H), 8.30 (s, 1H), 8.09 (d, J=5.0 Hz, 1H), 7.75 (t, J=5.0 Hz, 1H), 7.43 (d, J=5.0 Hz, 1H), 7.35 (s, 1H), 2.51 (s, 6H); $^{13}$C NMR (125 MHz, DMSO-d$_6$): δ 180.55, 175.18, 160.98, 160.40, 158.41, 138.94, 138.40, 136.74, 134.42, 131.31, 128.48, 126.67, 123.96, 118.61, 118.42, 115.47, 109.21, 67.08, 23.42.

Example 2

Synthesis of 4-(3-(6-cyano-5-(trifluoromethyl)pyridin-3-yl)-5,5-dimethyl-4-oxo-2-thioimidazolidine-1-yl)-2-fluoro-N-hydroxybenzamide (compound Zeta 33)

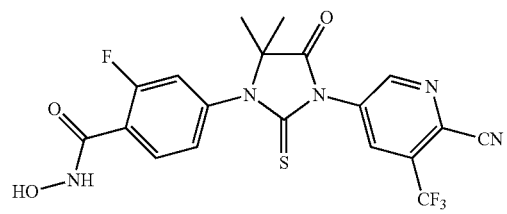

(1) Synthesis of 4-(3-(6-cyano-5-(trifluoromethyl)pyridin-3-yl)-5,5-dimethyl-4-oxo-2-thioimidazolidine-1-yl)-2-methyl fluorobenzoate 25

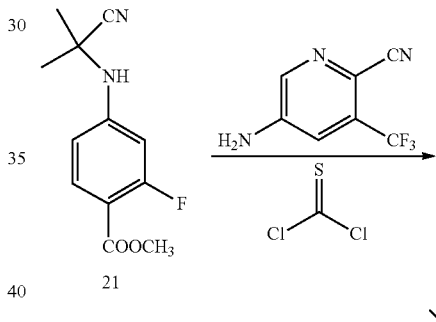

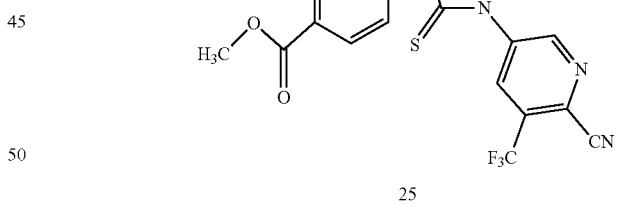

In a 25 mL two-necked flask, Compound 21 (0.60 g, 2.5 mmol), 3-chloro-4-cyanoaniline (0.561 g, 3 mmol), 8 mL of N, N-dimethylacetamide and thiophosgene (0.35 ml, 3.8 mmol) are added, temperature is risen to 70° C. and the reaction is performed for 24 h, and then the mixture was cooled to room temperature, 4 mL of methanol, 1 mL of concentrated hydrochloric acid and 2 mL of water are added, refluxing and stirring are preformed for 2 h, after it is cooled to the room temperature, ethyl acetate (20×3 mL) are used for extracting, the anhydrous sodium sulfate are used for drying, solvent is removed under a reduced pressure, the residue is purified by column chromatography to obtain Compound 25 (0.355 g, yellow solid) with a yield of 30.5%.

(2) Synthesis of 4-(3-(6-cyano-5-(trifluoromethyl)pyridin-3-yl)-5,5-dimethyl-4-oxo-2-thioimidazolidine-1-yl)-2-fluorobenzoic acid 26

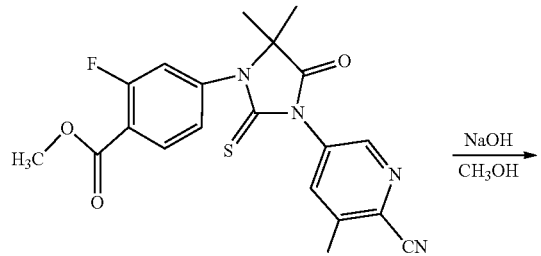

25

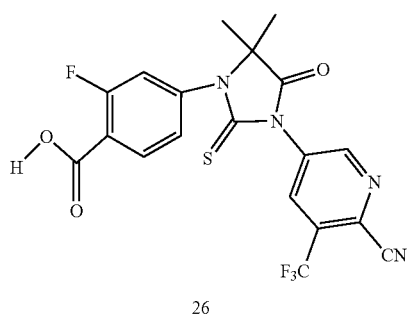

26

In a 25 mL two-necked flask, Compound 25 (0.230 g, 0.5 mmol) is dissolved in 2 mL of methanol, and 2 mL of 1 mol/L sodium hydroxide is added to the mixture, and stirring is performed at 20° C. for 4 h, After reaction completed, 2 mol/L of dilute hydrochloric acid is added to adjust a pH to 4, ethyl acetate (20 mL×3 mL) is used for extracting, anhydrous sodium sulfate is used for drying, solvent is removed under a reduced pressure to obtain Compound 26 (0.220 g, pale yellow solid) with a yield of 98.1%.

(3) Synthesis of 4-(3-(6-cyano-5-(trifluoromethyl)pyridin-3-yl)-5,5-dimethyl-4-oxo-2-thioimidazolidine-1-yl)-2-fluoro-N-hydroxybenzamide 27

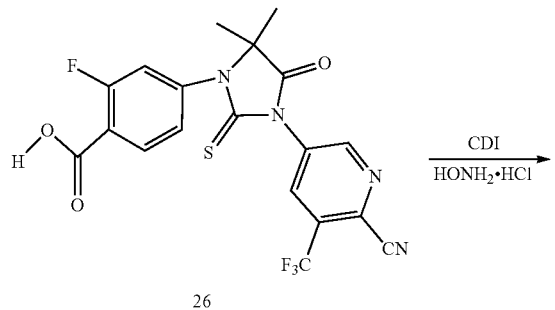

26

-continued

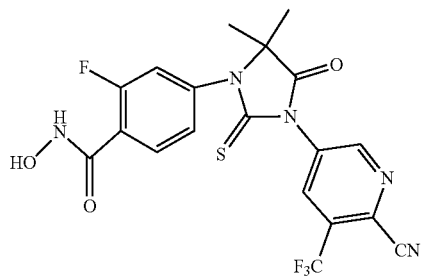

27

In a 25 mL two-necked flask, Compound 26 (0.200 g, 0.44 mmol), 4 mL of THF and CDI (0.143 g, 0.88 mmol) are successively added, after stirring is performed at 30° C. for 10 h, hydroxylamine hydrochloride (0.092 g, 1.32 mmol) is added. The reaction is performed at the room temperature for 10 h, monitored by TLC (ethyl acetate:petroleum ether:methanol=20:5:2). After the reaction completed, 4 mL of water is added, the ethyl acetate (10×3 mL) is used for extracting, anhydrous sodium sulfate is used for drying, and solvent is removed under a reduced pressure. The residue is purified by silica gel column chromatography to obtain a compound A8 (0.064 g, pale yellow solid) with a yield of 31.6%.

M.W.: 467.40; $^1$H NMR (500 MHz, CDCl$_3$): δ 8.95 (d, J=1.0 Hz, 1H), 8.46 (d, J=2.0 Hz, 1H), 7.85 (t, J=9.0 Hz, 1H), 7.38 (t, J=9.5 Hz 2H), 1.61 (s, 1H); $^{13}$C NMR (125 MHz, CD3OD): δ 180.63, 175.26, 162.16, 158.77, 151.31, 139.59, 135.87, 130.85, 126.25, 123.76, 112.21, 122.09, 118.34, 118.15, 66.78, 22.34.

Example 3

Synthesis of 4-(3-(3-chloro-4-cyanophenyl)-5,5-dimethyl-4-oxo-2-thioimidazolidine-1-yl)-2-fluoro-N-hydroxybenzamide (Zeta 34)

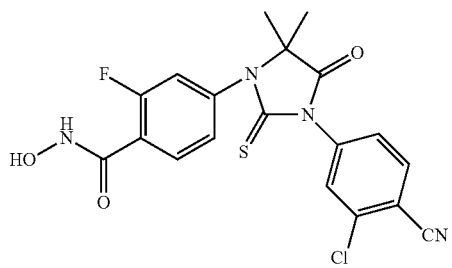

Zeta 34

(1) Synthesis of 4-((2-cyanoprop-2-yl)amino)-2-fluorobenzoic acid methyl ester 21

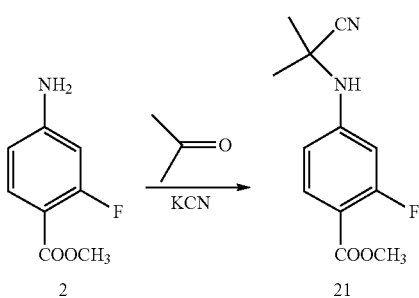

In a 150 mL two-necked flask, 2-fluoro-4-aminobenzoate 2 (4.5 g, 26.6 mmol), acetone (2.99 g, 42.7 mmol), potassium cyanide (2.6 g, 40 mmol) and 46 mL of acetic acid are successively added at room temperature, the mixed solution is heated to 75° C. and reacted for 24 h, the reaction is monitored by TLC (petroleum ether:ethyl acetate=20:3). After the reaction is completed, 20 mL of water is added, ethyl acetate (40×3 mL) is added for extracting, solvent removed under reduced pressure, residue heated to dissolve by adding a mixed solvent of 6 mL ethanol and 5 mL water, then cooled and crystallized, and filtered to obtain the compound 21 (3.13 g, yellow solid) with a yield of 50.2%.

(2) Synthesis of 4-(3-(3-chloro-4-cyanophenyl)-5,5-dimethyl-4-oxo-2-thioimidazolidine-1-yl)-2-methyl fluorobenzoate 22

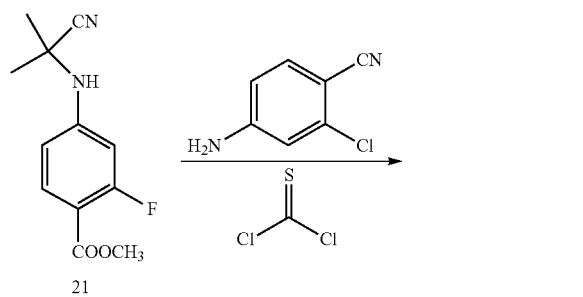

In a 25 mL two-necked flask, Compound 21 (0.500 g, 2.1 mmol), 3-chloro-4-cyanoaniline (0.38 g, 2.5 mmol) and 8 mL of N, N-dimethylacetamide are added, and then dropwise added thiophosgene (0.25 ml, 3.89 mmol). Temperature is risen to 95° C. and reaction performed for 24 h. After cooled to room temperature, 2 mL of methanol, 0.5 mL of concentrated hydrochloric acid and 2 mL of water are added, refluxing and stirring are performed for 2 h. After cooled to the room temperature, the mixture is extracted with ethyl acetate (10×3 mL), dried with anhydrous sodium sulfate, vacuumized to remove solvent, and then the residue is purified by column chromatography to obtain the compound 22 (0.257 g, yellow solid) with a yield of 28.8%.

(3) Synthesis of 4-(3-(3-chloro-4-cyanophenyl)-5,5-dimethyl-4-oxo-2-thioimidazolidine-1-yl)-2-fluorobenzoic acid 23

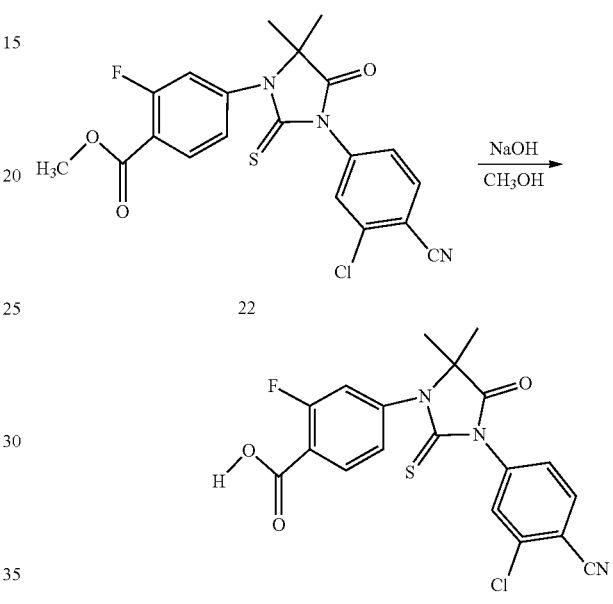

In 25 mL of a two-necked flask, the compound 22 (0.120 g, 0.28 mmol), 1 mL of methanol and 1 mL of 1 mol/L sodium hydroxide solution are added, stirring is performed at 20° C. for 4 h, after a reaction is completed, 2 mol/L dilute hydrochloric acid is added to adjust a pH to 4, the ethyl acetate (10×3 mL) is used for extracting, and the anhydrous sodium sulfate is used for drying, a solvent is removed under a reduced pressure to obtain the compound 23 (0.140 g, pale yellow solid) with a yield of 98.2%.

(4) Synthesis of 4-(3-(3-chloro-4-cyanophenyl)-5,5-dimethyl-4-oxo-2-thioimidazolidine-1-yl)-2-fluoro-N-hydroxy benzamide 24

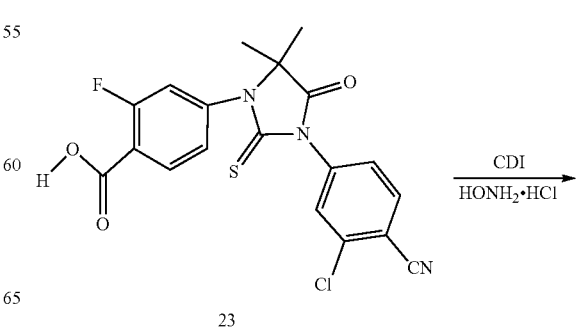

17
-continued

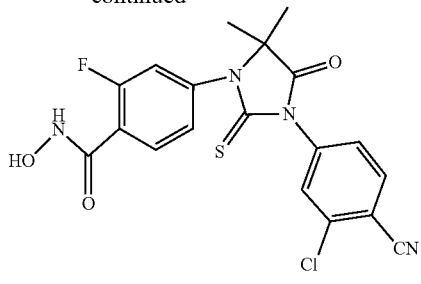

24

In a 25 mL two-necked flask, Compound 23 (0.120 g, 0.29 mmol), 4 mL of THF and CDI (0.093 g, 0.58 mmol) are added, after stirring is performed at 30 DEG C. for 10 h, hydroxylamine hydrochloride (0.060 g, 0.87 mmol) is added, and reaction is performed at room temperature for 10 h, monitored by TLC (ethyl acetate:petroleum ether:methanol=20:5:2). After the reaction completed, the mixture is added 4 mL of water, extracted with ethyl acetate (10×3 mL), dried with anhydrous sodium sulfate, and vacuumized to remove solvent. The residue is purified by silica gel column chromatography to obtain Compound 24 (0.038 g, pale yellow solid) with a yield of 30.5%.

M.W., 432.85; $^1$H NMR (500 MHz, CD$_3$OD): δ 7.97 (t, J=7.5 Hz, 1H), 7.82 (d, J=9.0 Hz 1H), 7.67 (s, 1H), 7.65 (dd, J=1.5 Hz, 1H), 7.37 (t, J=10.0 Hz, 2H), 1.60 (s, 6H)$^{13}$C NMR (125 MHz, CD$_3$OD): δ 180.46, 175.10, 162.24, 160.76, 138.53, 136.14, 134.12, 130.77, 130.39, 128.13, 126.16, 122.47, 119.94, 118.30, 114.87, 113.02, 66.57, 22.32.

Example 4

Synthesis of 4-(7-(4-cyano-3-(trifluoromethyl)phenyl)-8-oxo-6-thio-5,7-diazaspiro[3.4]octane-5-yl)-2-fluoro-N-hydroxybenzamide (Compound Zeta 55)

Zeta 55

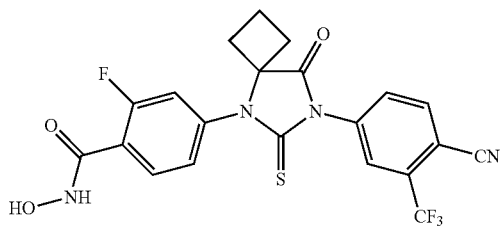

(1) Synthesis of 2-fluoro-4-methyl aminobenzoate 2

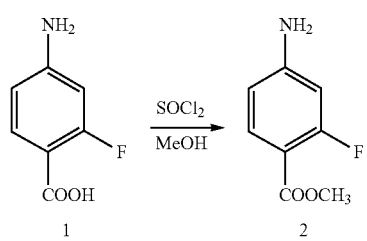

In a 100 mL two-necked flask, 2-fluoro-4-aminobenzoic acid 1 (10.00 g, 64.5 mmol) and 30 mL of methanol are added, 6.7 mL (92.0 mmol) of thionyl chloride is dropwise added into this solution under ice bath, and then the temperature is risen until refluxing. The reaction is performed for 3 hours, After the reaction solution is cooled to the room temperature, 20% of sodium carbonate solution is added to adjust pH to 8, ethyl acetate (30×3 mL) added for extracting, saturated sodium chloride solution used for washing, and anhydrous sodium sulfate used for drying, and then the solvent is removed under a reduced pressure to obtain the compound 2 (10.36 g, brown solid) with a yield of 95.5%.

(2) Synthesis of 4-((1-cyanocyclobutyl)amino)-2-methyl fluorobenzoate 3

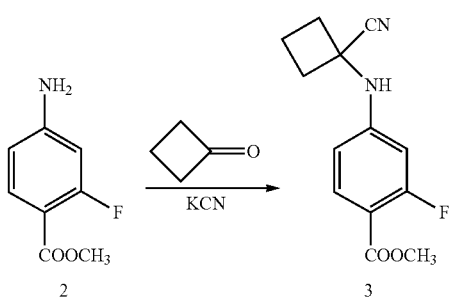

Into a 250 mL two-necked flask, 2-fluoro-4-aminobenzoic acid methyl ester 2 (3.70 g, 21.8 mmol), cyclobutanone (2.44 g, 34.8 mmol), potassium cyanide (2.12 g, 32.6 mmol) and 37 mL of acetic acid are added, the temperature is risen to 80° C. and the reaction is performed for 12 h, monitored by TLC (petroleum ether:ethyl acetate=20:3). After the reaction is completed, the mixture is added 20 mL of water, extracted with ethyl acetate (30×3 mL), and vacuumized to remove solvent obtaining the compound 3 (5.01 g, brown-red solid) with a yield of 92.5%.

(3) Synthesis of (7-(4-cyano-3-(trifluoromethyl)phenyl)-8-oxo-6-thio-5,7-diazaspiro[3.4]octane-5-yl)-2-methyl fluorobenzoate 4

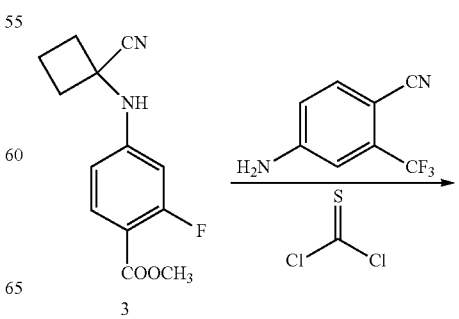

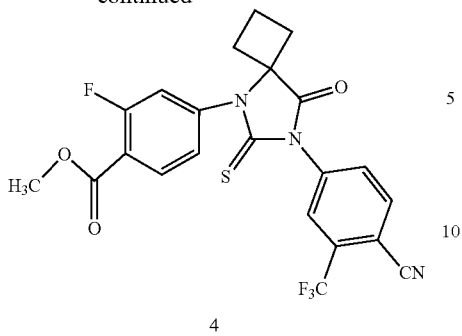

4

Into a 25 mL two-necked flask, Compound 3 (0.485 g, 1.95 mmol), 3-trifluoromethyl-4cyanoaniline (0.435 g, 2.34 mmol) and 6 mL of N,N-dimethylacetamide are added. After stirring is performed to dissolve, thiophosgene (0.25 ml, 2.96 mmol) is dropwise added, temperature is risen to 70° C. and the reaction is performed for 24 h. After cooled to the room temperature, 2 mL of methanol, 0.5 mL of concentrated hydrochloric acid and 2 mL of water are added, refluxing and stirring are performed for 2 h. after cooled to the room temperature, the mixture is extracted with ethyl acetate (10×3 mL), dried with anhydrous sodium sulfate, vacuumized to remove the solvent. The residue is purified by column chromatography to obtain the compound 4 (0.281 g, yellow solid) with a yield of 30.2%.

(4) Synthesis of (7-(4-cyano-3-(trifluoromethyl)phenyl)-8-oxo-6-thio-5,7-diazaspiro[3.4]octane-5-yl)-2-fluorobenzoic acid 5

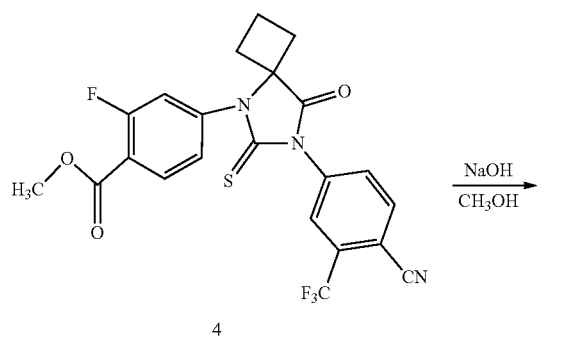

4

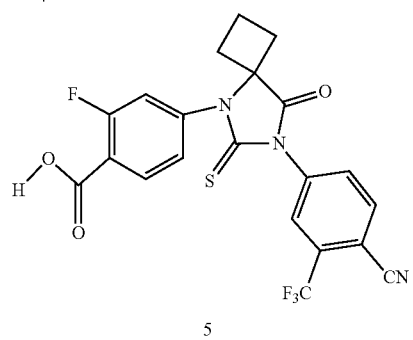

5

Into a 25 mL two-neck flask, Compound 4 (0.30 g, 0.62 mmol) and 2.5 mL of methanol are added, and 2.5 mL of 1 mol/L sodium hydroxide solution is added to this mixture, stirring is performed at 20° C. for 4 h. After the reaction is completed, 2 mol/L dilute hydrochloric acid is added to adjust pH to 4. The mixture is extracted with ethyl acetate (20×3 mL), dried with anhydrous sodium sulfate and vacuumized to remove solvent, obtaining Compound 5 (0.281 g, pale yellow solid) with a yield of 98.2%.

(5) Synthesis of 4-(7-(4-cyano-3-(trifluoromethyl)phenyl)-8-oxo-6-thio-5,7-diazaspiro[3.4]octane-5-yl)-2-fluoro-N-hydroxybenzamide 6

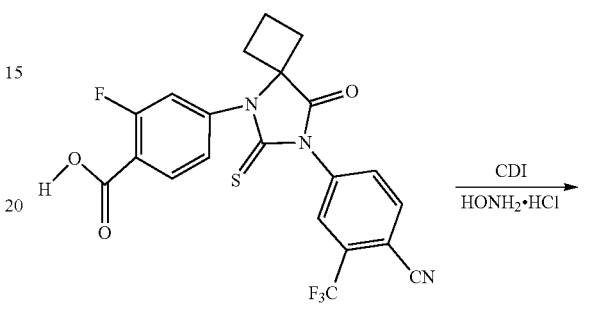

5

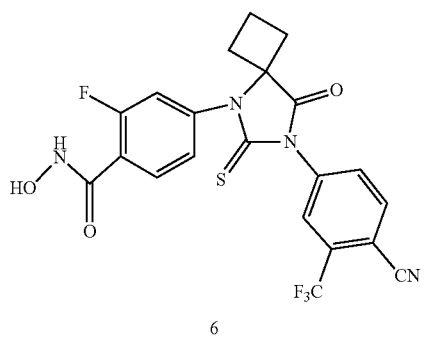

6

In a 25 mL two-necked flask, Compound 5 (0.181 g, 0.4 mmol), CDI (0.130 g, 0.8 mmol) and 10 mL of THF are successively added. After stirring is performed at 30° C. for 10 h, hydroxylamine hydrochloride (0.083 g, 1.2 mmol) is added. The reaction is performed at 25° C. for 10 h, monitored by TLC, (ethyl acetate:petroleum ether:methanol=20:5:2). After the reaction completed, 5 mL of water is added, and the mixture is extracted with ethyl acetate (10×3 mL), dried with anhydrous sodium sulfate, and vacuumized to remove solvent. The residue is purified by silica gel column chromatography to obtain a compound A5 (0.579 g, pale yellow solid) with a yield of 30.3%.

M.W., 478.42; $^1$H NMR (500 MHz, CD3OD): δ 8.15 (d, J=5.0 Hz, 2H), 7.98-7.96 (m, 1H), 7.88 (t, J=5.0 Hz, 1H), 7.39 (t, J=5.0 Hz, 2H), 2.71-2.66 (m, 2H), 2.59-2.53 (m, 2H), 2.15-2.09 (m, 1H), 1.66-1.60 (m, 1H) $^{13}$C NMR (125 MHz, CD3OD): δ 180.48, 175.00, 162.17, 158.90, 139.70, 137.98, 135.39, 133.42, 132.98, 131.01, 127.34, 126.70, 118.74, 118.54, 114.59, 109.28, 108.91, 67.74, 31.19.

Example 5

4-(7-(6-cyano-5-(trifluoromethyl)pyridin-3-yl)-8-oxo-6-thio-5,7-diazaspiro[3.4]octane-5-yl)-2-fluoro-N-hydroxybenzamide (Zeta 57)

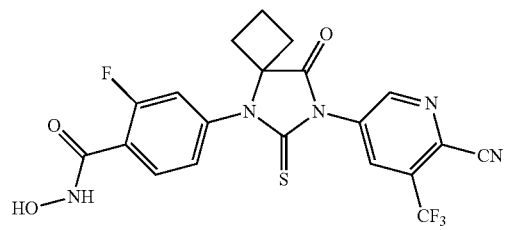

Zeta 57

(1) Synthesis of 4-(7-(6-cyano-5-(trifluoromethyl)pyridin-3-yl)-8-oxo-6-thio-5,7-diazaspiro[3.4]octane-5-yl)-2-fluorobenzoic acid methyl ester 10

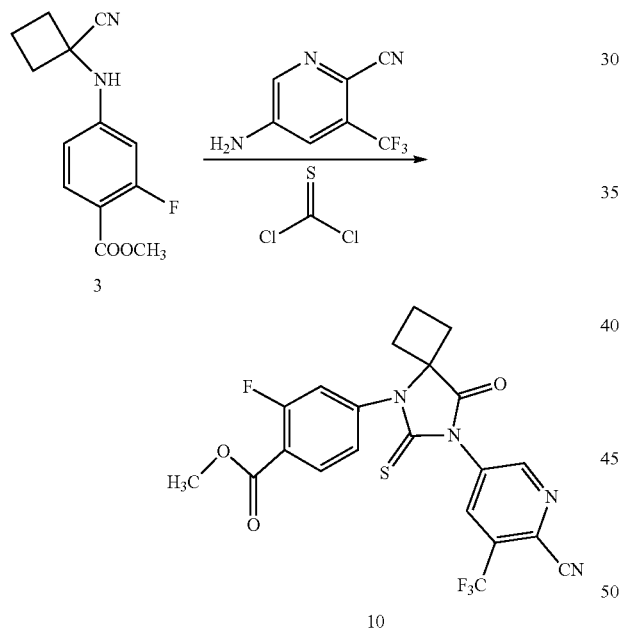

In a 25 mL two-necked flask, Compound 3 (0.50 g, 2.0 mmol), 3-trifluoromethyl-4cyanoaniline (0.448 g, 2.40 mmol) and 6.5 mL of N,N-dimethylacetamide are added, thiophosgene (0.28 ml, 3.20 mmol) is dropwise added to this solution. The temperature is risen to 70° C. and the reaction is performed for 24 h. After cooled to the room temperature, 2 mL of methanol, 0.5 mL of concentrated hydrochloric acid and 2 mL of water are added, refluxing and stirring are performed for 2 h. After cooled to the room temperature, the mixture is extracted with ethyl acetate (10×3 mL), dried with anhydrous sodium sulfate, and vacuumized to remove solvent. The residue is purified by column chromatography to obtain the compound 5 (0.286 g, pale yellow solid) with a yield of 29.9%.

(2) Synthesis of 4-(7-(6-cyano-5-(trifluoromethyl)pyridin-3-yl)-8-oxo-6-thio-5,7-diazaspiro[3.4]octane-5-yl)-2-fluorobenzoic acid 11

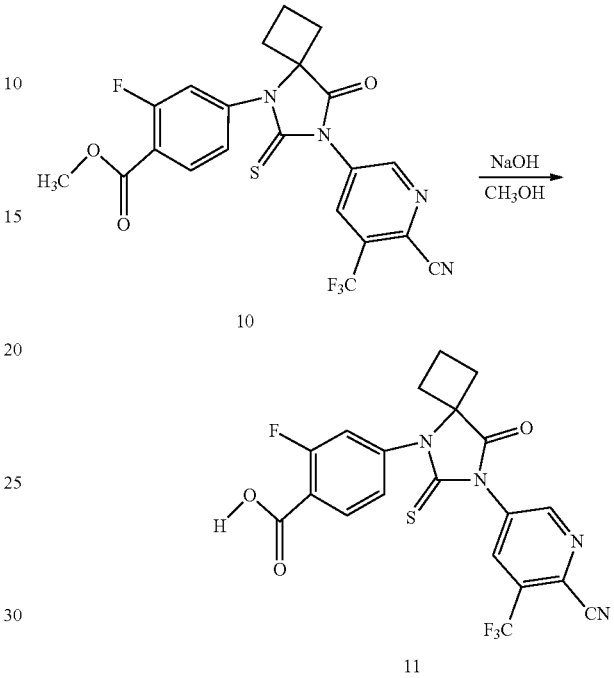

In a 25 mL of two-necked flask, Compound 10 (0.12 g, 0.25 mmol) and 1 mL of methanol are added, 1 mL of 1 mol/L sodium hydroxide is added to this mixture, stirring is performed overnight at 20° C., 2 mol/L dilute hydrochloric acid is added to adjust pH to 4. The mixture is extracted with ethyl acetate (10×3 mL), dried with anhydrous sodium sulfate, and vacuumized to remove solvent obtaining Compound 11 (0.113 g, pale yellow solid) with a yield of 97.1%.

(3) Synthesis of 4-(7-(6-cyano-5-(trifluoromethyl)pyridin-3-yl)-8-oxo-6-thio-5,7-diazaspiro[3.4]octane-5-yl)-2-fluoro-N-hydroxybenzamide 12

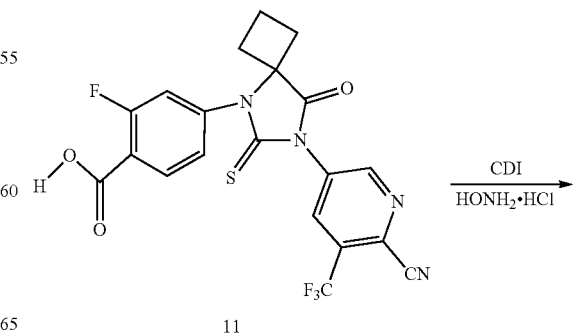

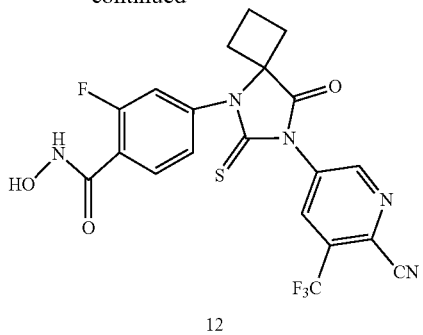

12

In a 25 mL two-necked flask, Compound 12 (0.097 g, 0.21 mmol), 2 mL of THF and CDI (0.068 g, 0.42 mmol) are added. After stirring at 30° C. for 10 h, hydroxylamine hydrochloride (0.044 g, 0.62 mmol) is added and the reaction is performed at 25° C. for 10 h, monitored by TLC (ethyl acetate:petroleum ether:methanol=20:5:2). After the reaction is completed, the mixture is added 2 mL of water, extracted with ethyl acetate (5×3 mL), dried with anhydrous sodium sulfate, and vacuumized to remove solvent. The residue is purified by silica gel column chromatography to obtain a compound A6 (0.031 g, pale yellow solid) with a yield of 31.2%.

M.W., 479.41; $^1$H NMR (500 MHz, CD3OD): δ 8.93 (s, 1H), 8.42 (s, 1H), 7.88 (t, J=7.0 Hz, 1H), 7.40 (t, J=10.5 Hz, 2H), 2.69 (s, 2H), 2.56 (d, J=10.0 Hz, 2H), 2.15-2.10 (d, 1H), 1.63 (d, J=9.5 Hz 1H), $^{13}$C NMR (125 MHz, CD3OD): δ 180.74, 175.18, 162.16, 158.91, 151.26, 150.86, 149.36, 139.70, 135.74, 131.03, 126.67, 125.74, 122.37, 122.24, 118.70, 118.51, 67.86, 31.19, 13.14.

Biological activity testing results of some compounds according to the disclosure are described below:

Reagents used:
DHT (dihydrotestosterone), provided by Sigma company, USA;
ARN509, synthesized by the inventor; and
MDV3100, synthesized by the inventor.

1. Test of AR Antagonistic Activity
1.1. Binding Experiment of the Antagonist and AR PolarScreen™ Androgen Receptor (AR) Competitor Assay, Green kit (Life technologies company, USA) is used to test the affinity of the antagonist to AR-LBD (GST). The mechanism of the experiment is that the AR-LBD is combined with a small molecule fluormone tracer (Fluormone Tracer), and an antagonist added can competitively bind with AR-LBD so as to replace the fluormone tracer, and the replaced fluormone tracer may produce fluorescence polarization, and the value of the fluorescence polarization is inversely proportional to the number of the replaced tracers.

A specific process is as follows: the drug is dissolved into 500 uM by using DMSO, and then diluted to 244 nM by double dilution concentration gradients in a 96-well plate. A 10 uL of a reaction system AR-LBD+Tracer is configured in a 384-well plate and 10 uL of the drug solution is added. The positive control is 10 uL of AR-LBD+Tracer with 10 uL of DHT added. The 384-well plate is wrapped by tin foil and incubated for 6 hours in the dark. The fluorescence polarization value is read on a multi-function microplate reader. Graphpad Prism software is used to draw a drug concentration as an abscissa, and the fluorescence polarization value is used as an ordinate for drawing a curve. FIG. 1 shows graphical representation of the $IC_{50}$ result of the drug and AR-LBD binding. Herein, the DHT, MDV3100, and ARN509 are positive controls.

It is observed from FIG. 1 that all of the synthesized drugs can bind to the AR in different degrees, herein binding forces of Zeta 32, Zeta 33 and Zeta 55 are superior, with IC50 being 25.05, 27.54, and 29.80 uM, respectively.

1.2. Luciferase Reporter Gene Experiment 293T cells are cultured in a 96-well plate. AR plasmids and luciferase genes with AR target promoters are co-transfected in the 293T cells. AR activates the target promoters to express luciferase, and the expression level of the luciferase is directly proportional to AR activation. Adding DHT to the cells can activate AR and express the luciferase, thus enhancing fluorescence signal detection. By detecting the fluorescent signal, it can be examined whether an added drug has AR antagonist activity.

The luciferase reporter gene plasmid MMTV-LUC containing the androgen receptor (AR) target promoters and the plasmid pSV-AR expressing the androgen receptor (AR) are constructed. The 293T cells are inoculated in a 96-well plate, wherein each well containing 1×10$^4$ cells. The cells are incubated overnight to stick to the wall. On the second day, Lipofectamine® 3000 (Life technologies, USA) is used to transfect the plasmid into the cells. Each well is added with 180 ng of MMTV-LUC plasmid and 20 ng of pSV-AR plasmid. On the third day, each well is added with 10 nM of the DHT and the drugs of different concentrations of 1 nM, 10 nM, 100 nM, 1 uM, 10 uM, 25 uM, 50 uM respectively. The control is 10 nM of the DHT. On the fifth day, a luciferase reporter gene detection kit (Biyuntian company, China) is used to process the cells. 100 uL of cell lysate is added to the 96-well plate, and lyse for 20 min. Then centrifuging is performed at 4 degrees and 10000 g for 3 min. 50 uL of supernatant is taken and 100 uL of a luciferase detection reagent is added. After mixing, chemiluminescence is immediately detected on the multi-functional microplate reader. Graphpad Prism software is used to draw a curve by using the drug concentration as an abscissa and using drug fluorescence value/positive control fluorescence value as an ordinate. Herein MDV3100 is the positive control.

It can be observed from FIG. 2 that all of the synthesized drugs have antagonist effects on the AR, and the antagonistic ability thereof from high to low is Zeta32>Zeta55>Zeta34>Zeta57>Zeta33.

1.3. AR and PSA Expression Detected by Western Blot VCaP Cells Test

VCaP cells are spread in a 6-well plate. 5×10$^5$ cells are incubated per well. The cells are incubated overnight to make the cells stick to the wall. On the second day, 10 uM of the drug is added to each well. After incubating for 24 h, the cells are collected, the cells are lysed to extract total proteins. Western Blot is used to detect an expression level of PSA in the cells after the different drugs are added, and a result is as shown in FIG. 3.

It can be observed from FIG. 3 that all of the synthesized drugs can significantly inhibit the expression of the downstream protein of the AR pathway (PSA), indicating that the synthesized drugs can inhibit a function of the AR.

2. Histone Deacetylase (HDAC) Inhibitory Activity

The VCap cells are cultured in the 6-well plate. After treating the VCap cells with the drugs for 24 hours, acetylation levels of the tubulin in the cytoplasm and the H3 protein in the nucleus are examined by the western blot. An experiment process is as follows:

The VCaP cells are spread in the 6-well plate. 5×10$^5$ cells are inoculated per well, and incubated overnight to make the cells stick to a wall. On the second day, 10 uM of the drug is added per well. After being incubated for 24 h, the cells are collected, and lysed to extract the cell total protein. The Western Blot method is used to detect the expression levels of Kac-tubilin (localized cytoplasm) in the cells after treating with the different drugs. An experiment result is as shown in FIG. 4, and Kac in the figure represents lysine acetylation.

The VCaP cells are spread in the 6-well plate. $5\times10^5$ cells are inoculated per well, and incubated overnight to make the cells stick to a wall. Then 10 uM of the drug is added to each well. The cells are collected after being incubated for 24 h. The EpiQuik Total Histone Extraction kit (Epigentek, USA) is used to extract the histones, and the Western Blot method is used to detect expression levels of Kac-H3 (localized cell nucleus) in the cells after adding the different drugs. An experiment result is as shown in FIG. 5.

It can be observed from FIG. 4 and FIG. 5 that all of the synthesized drugs have certain degree of histone deacetylase (HDAC) inhibitory activity, and can enhance acetylation of the tubulin proteins and the histones. For acetylation of the tubulin in the cytoplasm, the activities of the Zeta32 and Zeta55 are superior (FIG. 4). For the H3 acetylation in the nucleus, the activities of the Zeta32, Zeta55, Zeta57 and Zeta34 are superior (FIG. 5).

MDA-MB-453 Cells Test

MDA-MB-453 cells treated with Zeta55 or Tubastatin A at indicated concentrations for 48 h were harvested and lysed in ice-cold RIPA buffer with protease inhibitor Cocktail. After quantification by BCA, protein (30-50 μg) were separated with 10% SDS-PAGE gels and transferred onto polyvinylidene difluoride (PVDF) membranes. The following antibodies were used in this study: AR(CST,1:1000),α-tubulin(CST,1:1000), Ac-α-tubulin(CST,1:1000). Secondary antibodies: HRP-conjugated anti-mouse IgG and anti-rabbit IgG (Proteintech, 1:5000).

FIG. 7 shows TNBC cell line MDA-MB-453 has high level expression of AR, similar to prostate cancer cell line Vcap and LNCap.

3. Measurement of Cell Proliferation Inhibitory Activity 3.1. Inhibiting Effect of the Drug on VCaP Cell Proliferation Androgen-sensitive prostate cancer cell (VCaP cells) are cultured in a 96-well plate. The VCaP cells are able to proliferate in a medium supplemented with 10 nM of the DHT. After treating the cells with the drugs for 4 days, we measure the effects of the drugs on the proliferation of the prostate cancer cells.

The VCaP cells are cultured by using 5% CSS and 1640 medium without phenol red, and inoculated in the 96-well plate. $1\times10^4$ cells are added to each well, and incubated overnight to make the cells stick to a wall. Different concentrations of the drugs are added on the second day. After treating the cells with the drugs for 4 days, cell viability is measured by the MTS kit (Promega, USA). To each well, 10% of an MTS reagent is added, and incubation continued for 2 hours. The absorbance value at 490 nM is then measured by the multi-functional microplate reader. The Graphpad Prism software is used to draw a curve by using the drug concentration as an abscissa and using the absorbance value of the drug treatment/the absorbance value of the blank treatment cell as an ordinate.

It can be observed from FIG. 6 that all of the synthesized drugs have the inhibitory effect on the VCap cell proliferation, and the inhibitory effect from high to low is Zeta55>Zeta32>Zeta33>Zeta34>Zeta57. Herein the cell proliferation inhibitory effects of the drugs Zeta55, Zeta32 and Zeta33 are better than that of the positive control drug MDV3100.

3.2 Inhabitation Effects of Drugs on Cell Proliferation of MDA-MB-453

8000 MDA-MB-453 cells were plated in each well of a 96-well plate and incubated for 48 hours. Then cells were treated with increasing concentrations of Zeta55, MDV3100 or SAHA for 72 h, At last, cell viability was measured using a CCK8 Assay kit.

Figure 9:
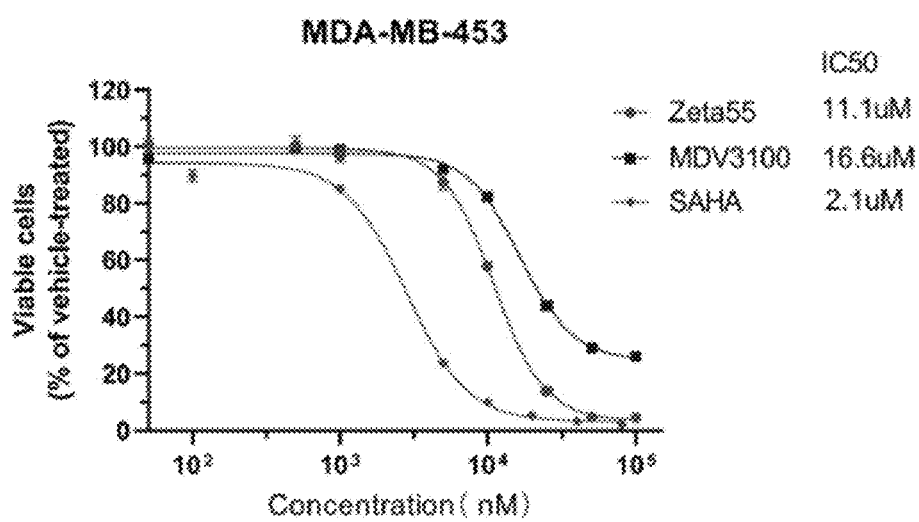

FIG. 8 shows that treatment of MDA-MB-453 TNBC cells with Zeta55 results in significant dose-dependent reduction of AR protein in MDA-MB-453 TNBC cells. FIG. 9 shows that treatment of MDA-MB-453 TNBC cells with Zeta55 results in dose-dependent killing of the cells with IC50 of 11.1 uM, about 1.5 times more potent than MDV3100

3.3. Selective Effects of the Drug to Cells 293T cells are AR-negative human embryonic kidney cells, DU145 cells are AR-negative prostate cancer cells, and VCaP cells are AR-positive prostate cancer cells. These three types of the cells are cultured in the 96-well plates and treated with the drugs (in the concentration gradient) respectively for 4 days. Then the inhibition of the drugs on cell proliferation are measure by MTS. Detailed process is as follows:

The VCaP cells are cultured with 5% CSS and 1640 medium without phenol red, and inoculated in the 96-well plates, and $1\times10^4$ cells are added to each well. The 293T cells and the DU145 cells are cultured with 10% FBS and 1640 medium, and inoculated in the 96-well plates, and $2\times10^3$ cells are added to each well. The cells are incubated overnight to make the cells stick to a wall. Then the different concentrations of the drugs are added on the second day. After treatment with the drugs for 4 days, cell viability is measured by the MTS kit (Promega, USA). To each well, 10% of an MTS reagent is added, and incubation continued for 2 hours. The absorbance value at 490 nM is then measured by the multi-functional microplate reader. The Graphpad Prism software is used to draw a curve by using the drug concentration as an abscissa and using the absorbance value of the drug treatment/the absorbance value of the blank treatment cell as an ordinate.

It can be observed from FIG. 10 that Zeta 55 has selective proliferation inhibition on the AR-positive VCaP cells. The proliferation inhibition effect of Zeta 55 on the AR-positive VCaP cells is more than 20 times greater than that on the AR-negative cells (293T and DU145). It is indicated that the Zeta 55 may have low cytotoxicity toward AR-negative cells.

What is claimed is:

1. A pharmaceutical compound, having a structure of Formula I:

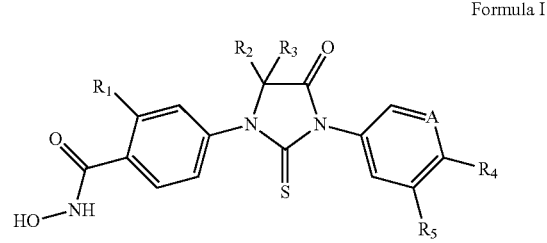

Formula I or a pharmaceutically acceptable salt thereof, wherein, R1 is selected from hydrogen, fluorine, and chlorine; R2 and R3 are independently selected from hydrogen, alkyl, a substituted alkyl, alkenyl or a substituted alkenyl, alkynyl or a substituted alkynyl, and aryl, or R2 and R3 are connected to form a ring which is selected from cycloalkyl, a substituted cycloalkyl, an aromatic heterocycle or a non-aromatic heterocycle; R4 is selected from hydrogen, cyano, alkyl, a substituted alkyl, alkenyl or a substituted alkenyl, alkynyl or a substituted alkynyl, and aryl; and R5 is selected from hydrogen, halogen, and haloalkyl.

2. The compound as claimed in claim 1, wherein, the R1 is hydrogen or fluorine.

3. The compound as claimed in claim 1, wherein, R2 and R3 are independently an alkyl of C1-C3, or combined to form a cycloalkyl of C3-C6.

4. The compound as claimed in claim 1, wherein, R4 is cyano.

5. The compound as claimed in claim 1, wherein, the R5 is trihalomethyl, preferably trifluoromethyl.

6. A pharmaceutical composition, containing a therapeutically effective amount of the compound or the pharmaceutically acceptable salt thereof as claimed in claim 1, and a pharmaceutically acceptable carrier.

7. A pharmaceutical composition, containing a therapeutically effective amount of the compound or the pharmaceutically acceptable salt thereof as claimed in claim 1, and a pharmaceutically acceptable diluent.

8. A pharmaceutical composition, containing a therapeutically effective amount of the compound or the pharmaceutically acceptable salt thereof as claimed in claim 1, and a pharmaceutically acceptable additive.

9. The pharmaceutical composition as claimed in claim 6, wherein the compound is the following compound,

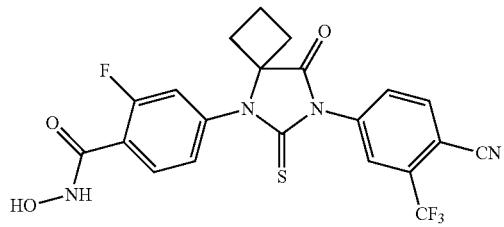 [SMILES: N#Cc1ccc(N2C(=O)C3(CCC3)N(c3ccc(C(=O)NO)c(F)c3)C2=S)cc1C(F)(F)F]

or a pharmaceutically acceptable salt thereof.

10. The pharmaceutical composition as claimed in claim 6, wherein the compound is the following compound

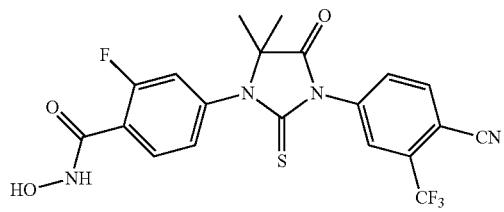 [SMILES: CC1(C)C(=O)N(c2ccc(C#N)c(C(F)(F)F)c2)C(=S)N1c1ccc(C(=O)NO)c(F)c1]

or a pharmaceutically acceptable salt thereof.

11. The pharmaceutical composition as claimed in claim 6, wherein the pharmaceutical composition is in the form of intravenous injection administration, tissue injection administration, intraperitoneal administration, oral administration, or intranasal administration.

* * * * *